US011058565B2

(12) United States Patent
Laramy et al.

(10) Patent No.: US 11,058,565 B2
(45) Date of Patent: *Jul. 13, 2021

(54) SYSTEM FOR DEPLOYING A SHAPE MEMORY CATHETERIZATION DEVICE WITH STRAIN FEEDBACK AND METHODS FOR USE THEREWITH

(71) Applicant: Memory Effect Medical, LLC, Austin, TX (US)

(72) Inventors: Christine Laramy, Austin, TX (US); Bruce Stuckman, Austin, TX (US)

(73) Assignee: Memory Effect Medical, LLC, Austin, TX (US)

( * ) Notice: Subject to any disclaimer, the term of this patent is extended or adjusted under 35 U.S.C. 154(b) by 677 days.

This patent is subject to a terminal disclaimer.

(21) Appl. No.: 15/956,025

(22) Filed: Apr. 18, 2018

(65) Prior Publication Data

US 2018/0228629 A1    Aug. 16, 2018

Related U.S. Application Data

(63) Continuation of application No. 13/956,536, filed on Aug. 1, 2013, now Pat. No. 9,974,673.

(Continued)

(51) Int. Cl.
*A61B 17/12* (2006.01)
*A61F 2/95* (2013.01)
(Continued)

(52) U.S. Cl.
CPC .......... *A61F 2/95* (2013.01); *A61B 17/12113* (2013.01); *A61B 17/12145* (2013.01);
(Continued)

(58) Field of Classification Search
CPC .... A61B 2017/00115; A61B 17/12113; A61B 17/12145; A61B 2017/00411;
(Continued)

(56) References Cited

U.S. PATENT DOCUMENTS 5,989,242 A * 11/1999 Saadat ............. A61B 17/12022
606/1
6,102,917 A * 8/2000 Maitland .......... A61B 17/12022
606/108

(Continued)

OTHER PUBLICATIONS

Maitland, Duncan J. et al; Design and Realization of Biomedical Devices Based on Shape Memory Polymers, Mater. Res. Soc. Symp. Proc. vol. 1190; 2009; 13 pages.

(Continued)

*Primary Examiner* — William R Carpenter
*Assistant Examiner* — William R Frehe
(74) *Attorney, Agent, or Firm* — Garlick & Markison; Bruce E. Stuckman

(57) ABSTRACT

A system for deploying a shape memory catheterization device within a patient, includes a catheter for endovascular insertion of the shape memory catheterization device. A heat source heats the shape memory catheterization device above the transition temperature. A transformation data generator includes a circuit driver for driving a circuit that includes at least one strain gage of the shape memory catheterization device and a detection circuit for generating transformation data based on a strain indicated by the at least one strain gage, wherein the transformation data indicates a shape transformation of the shape memory catheterization device from a catheterization shape to a transformed shape.

10 Claims, 15 Drawing Sheets

Related U.S. Application Data

(60) Provisional application No. 61/754,473, filed on Jan. 18, 2013.

(51) Int. Cl.
*A61M 25/00* (2006.01)
*A61N 1/40* (2006.01)
*A61B 17/00* (2006.01)

(52) U.S. Cl.
CPC ......... *A61M 25/0043* (2013.01); *A61N 1/406* (2013.01); *A61B 2017/00115* (2013.01); *A61B 2017/00411* (2013.01); *A61B 2017/00867* (2013.01); *A61B 2017/00871* (2013.01); *A61B 2017/12077* (2013.01); *A61F 2002/9505* (2013.01); *A61F 2250/0001* (2013.01); *A61F 2250/0067* (2013.01); *A61M 2025/0064* (2013.01)

(58) Field of Classification Search
CPC ........... A61B 2017/00867; A61B 2017/00871; A61B 2017/12077; A61M 25/0043; A61M 2025/0064; A61N 1/406; A61F 2/95; A61F 2002/9505; A61F 2250/0001; A61F 2250/0067

See application file for complete search history.

(56) References Cited

U.S. PATENT DOCUMENTS

| | | | |
|---|---|---|---|
| 7,604,398 B1 | 10/2009 | Akers | |
| 7,834,471 B2 * | 11/2010 | Cripps | .................. F03G 6/001 290/1 E |
| 7,857,642 B1 | 12/2010 | Manes | |
| 8,382,834 B2 | 2/2013 | Prescott | |
| 9,078,481 B2 * | 7/2015 | Howard | ................ H02J 7/0027 |
| 10,463,516 B2 * | 11/2019 | Laramy | .................... A61F 2/95 |
| 2003/0236533 A1 | 12/2003 | Wilson | |
| 2005/0033163 A1 | 2/2005 | Duchon | |
| 2006/0095103 A1 | 5/2006 | Eggers | |
| 2007/0121230 A1 | 5/2007 | Klein | |
| 2008/0167641 A1 | 7/2008 | Hansen | |
| 2009/0076597 A1 * | 3/2009 | Dahlgren | .......... A61B 17/7016 623/2.1 |
| 2009/0218321 A1 | 9/2009 | Ashman | |
| 2011/0144686 A1 | 6/2011 | Wilson | |
| 2011/0178380 A1 | 7/2011 | Chowdhury | |
| 2011/0251687 A1 | 10/2011 | Prescott | |
| 2012/0041470 A1 | 2/2012 | Shrivastava | |

OTHER PUBLICATIONS

Sokolowski, Witold et al.; Medical Applications of Shape Memory Polymers; Mar. 2, 2007; 10 pages.

\* cited by examiner

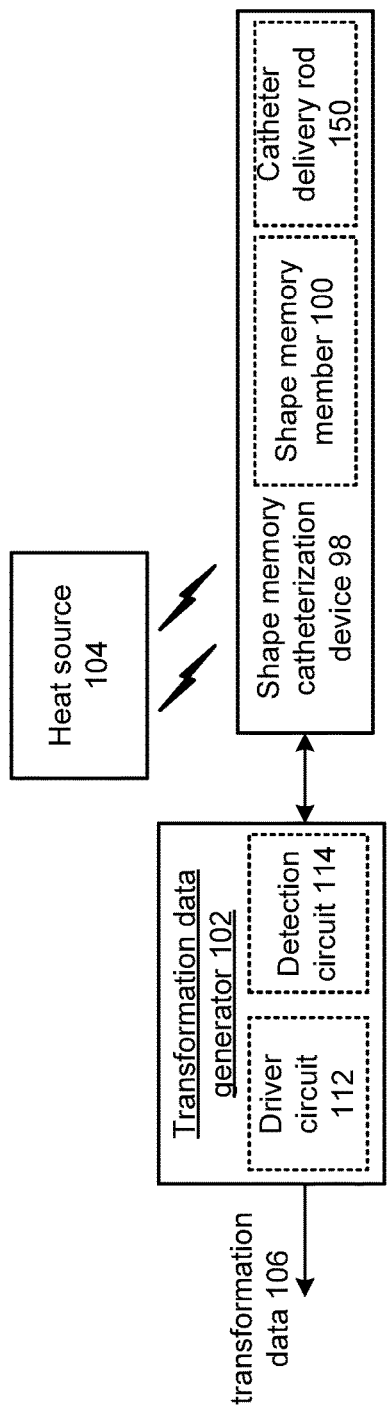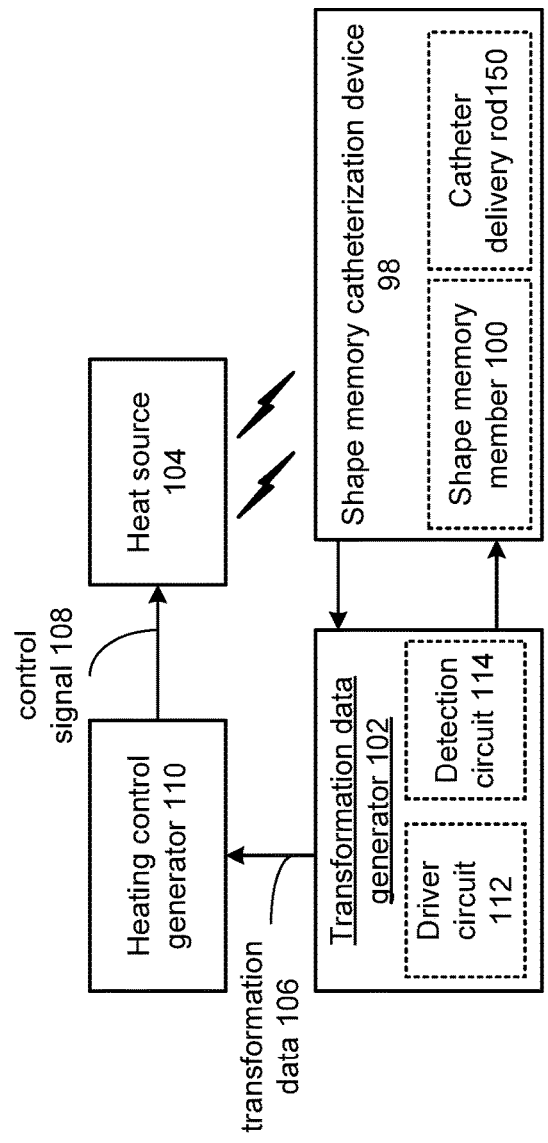

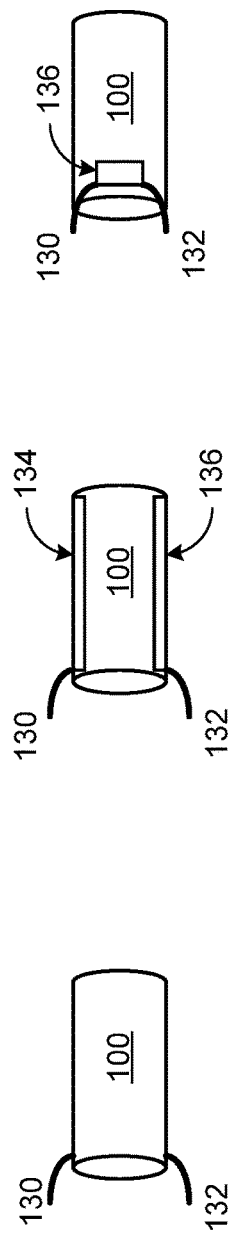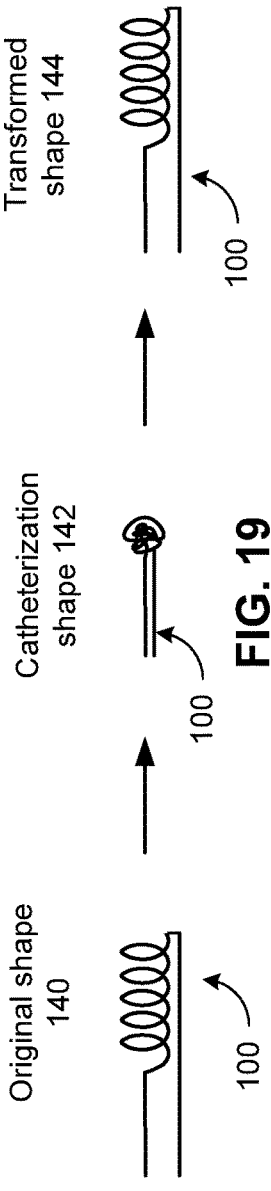

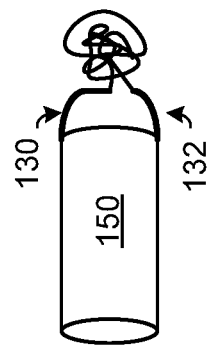
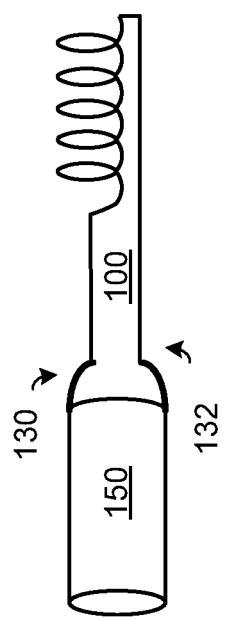
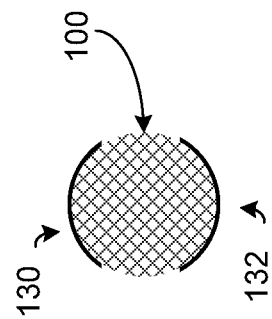

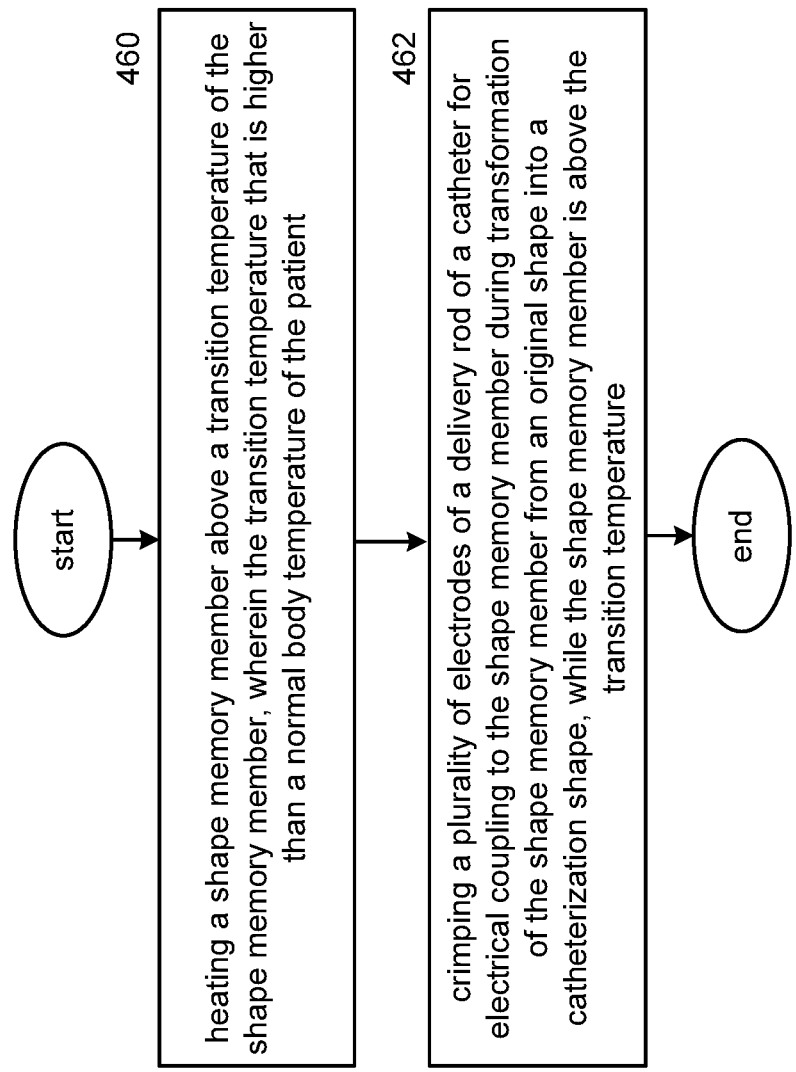

they hereby incorporated herein by reference in their entirety and made part of the present U.S. Utility Patent Application for all purposes.

SYSTEM FOR DEPLOYING A SHAPE MEMORY CATHETERIZATION DEVICE WITH STRAIN FEEDBACK AND METHODS FOR USE THEREWITH

CROSS REFERENCE TO RELATED PATENTS

The present U.S. Utility Patent Application claims priority pursuant to 35 U.S.C. § 120 as a continuation of U.S. Utility application Ser. No. 13/956,536, entitled "SYSTEM FOR DEPLOYING AN INDUCTIVE SHAPE MEMORY CATHETERIZATION DEVICE AND METHODS FOR USE THEREWITH", filed Aug. 1, 2013, which claims priority pursuant to 35 U.S.C. § 119(e) to U.S. Provisional Application No. 61/754,473, entitled "SHAPE MEMORY CATHETERIZATION DEVICE WITH ELECTRICAL TRANSFORMATION FEEDBACK AND METHODS FOR USE THEREWITH", filed Jan. 18, 2013, both of which are hereby incorporated herein by reference in their entirety and made part of the present U.S. Utility Patent Application for all purposes.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to medical devices that intravenously insert shape memory members in a patient.

DESCRIPTION OF RELATED ART

A wide range of medical treatments can be performed with a catheter that is intravenously inserted in a patient. Such catheterizations have reduced invasiveness compared with conventional treatments leading to lower risk to the patient, faster healing times, etc. Shape memory devices that change shape based on temperature have been used in such catheterizations. These devices can be lightweight and biocompatible.

The disadvantages of conventional approaches will be evident to one skilled in the art when presented the disclosure that follows.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWING(S)

FIG. 1 is a schematic block diagram of an embodiment of a system for deploying a shape memory catheterization device 98 in accordance with the present invention;

FIG. 2 is a schematic block diagram of an embodiment of a system for deploying a shape memory catheterization device 98 in accordance with the present invention;

FIG. 16 is a pictorial representation of the transformation of a shape memory member of in accordance with an embodiment the present invention;

FIG. 17 is a pictorial representation of the transformation of a shape memory member of in accordance with an embodiment the present invention;

FIG. 18 is a pictorial representation of the transformation of a shape memory member of in accordance with an embodiment the present invention;

FIG. 19 is a pictorial representation of the transformation of a shape memory member of in accordance with an embodiment the present invention;

FIG. 20 is a pictorial representation of the transformation of a shape memory member of in accordance with an embodiment the present invention;

FIG. 21 is a pictorial representation of a shape memory member and catheter in accordance with an embodiment the present invention;

FIG. 22 is a pictorial representation of a shape memory member and catheter in accordance with an embodiment the present invention;

FIG. 23 is a pictorial representation of a shape memory member and catheter in accordance with an embodiment the present invention;

FIG. 30 is a flowchart representation of an embodiment of a method in accordance with the present invention.

DETAILED DESCRIPTION OF THE INVENTION

Figure 4:
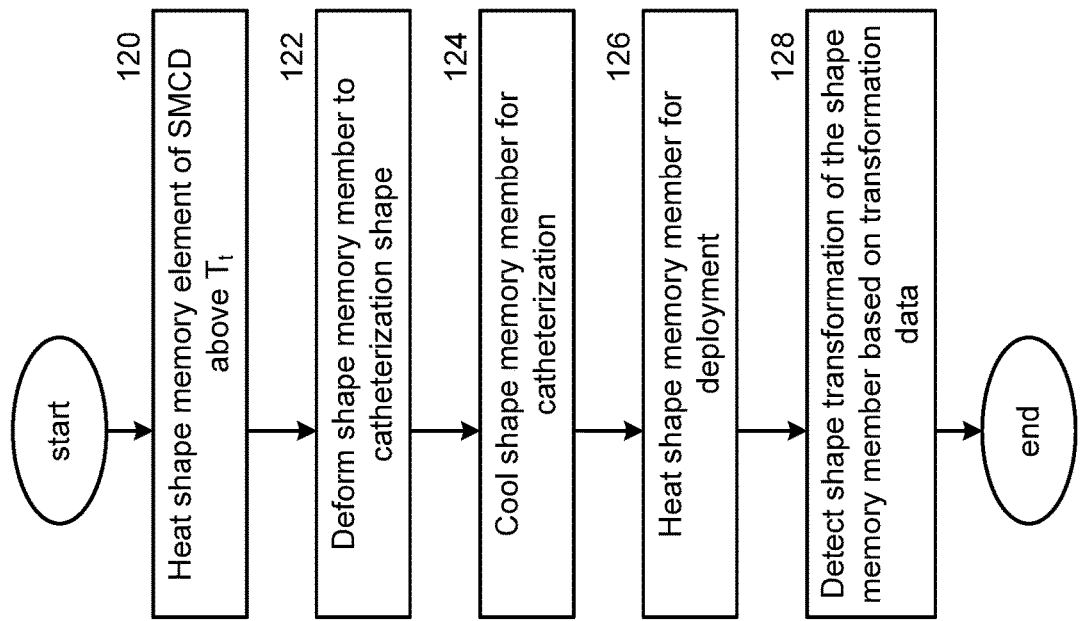
FIG. 4 is a flow diagram of an embodiment of a method in accordance with the present invention.

FIG. 1 is a schematic block diagram of an embodiment of a system for deploying a shape memory catheterization device 98 in accordance with the present invention. In particular, a shape memory catheterization device 98 includes a catheter having a delivery rod 150 for use in conjunction with a catheterization procedure involving the insertion of the shape memory catheterization device 98 into a patient. Examples of such catheterization procedures include the insertion of an endovascular stent as part of an angioplasty or treatment of an aneurism or the intravenous deployment of another medical device, an intravenous drug deployment or the administration of anesthetic medication into the epidural space, the subarachnoid space, or around a major nerve bundle such as the brachial plexus, the administration of anesthetic medication into the epidural space, the subarachnoid space, or around a major nerve bundle such as the brachial plexus, an in vitro fertilization or other medical treatment, a urinary catheterization, treatment of an abdominal abscess, a balloon septostomy, balloon sinuplasty, catheter ablation, an in vitro fertilization or other medical treatment.

The shape memory catheterization device 98 includes a shape memory member 100 having a transition temperature that is higher than a normal body temperature of the patient. When heat is applied by a heat source 104 the shape memory member 100 of shape memory catheterization device 98 is heated above the transition temperature causes the shape memory member 100 to undergo a shape transformation from a catheterization shape into a transformed shape that is useful in the particular treatment. The heat source 104 can be an infrared emitter, laser or other light source, a heating coil or other electrical heating source, a microwave source or other electromagnetic source, a radiation source or other heat source. While shown separately from the shape memory catheterization device 98, the heat source 104 can be integrated into the shape memory catheterization device 98.

A transformation data generator 102 includes a circuit driver 112 for driving a circuit that includes at least one electrical element of the shape memory member 100 via a signal line included in the delivery rod and a plurality of electrodes that couple to the shape memory device 100. The transformation data generator 102 also includes a detection circuit 114 for generating transformation data 106 based on feedback generated by the detection circuit 114. The transformation data 106 indicates a shape transformation of the shape memory member 100 of the shape memory catheterization 98 device from the catheterization shape to the transformed shape. In an embodiment of the present invention the transformation data 106 can be displayed or otherwise used to provide visual, audible or tactile feedback to the users of shape memory catheterization device 98 that the shape memory member 100 has reached its transformation shape.

Further examples including numerous optional functions and features of shape memory catheterization device 98 are discussed in conjunction with FIGS. 2-30 that follow.

FIG. 2 is a schematic block diagram of an embodiment of a system for deploying a shape memory catheterization device 98 in accordance with the present invention. In particular, a system is shown that includes many common elements of those described in conjunction with FIG. 1 that are referred to by common reference numerals. In addition, a heating control generator 110 is included that generates a control signal 108 for controlling the heat source 104 based on the transformation data 106. In operation, the heating control generator generates the control signal 108 to discontinue the heating of the shape memory catheterization device 98 when the transformation data 106 indicates the shape transformation of the shape memory member 100 from the catheterization shape to the transformed shape.

In an example of operation, the shape memory member 100 is a shape memory polymer, alloy or other device with a transition temperature that is slightly above the body temperature of the patient. The shape memory member 100 is heated above the transition temperature to effectuate the shape transformation of the shape memory member as part of the treatment. Overheating of blood or tissue can cause undesirable blood clotting during a treatment or other harmful effects. Discontinuing heating by heat source 104 after the shape transformation has occurred can avoid overheating the patient's tissue, blood and other body fluids during the procedure and allows the users of shape memory catheterization device to provide only as much heat as is reasonably necessary to effectuate the shape transformation.

Heating control generator 110 can be implemented using a processing device such as shared processing device, individual processing devices, or a plurality of processing devices and may further include memory. Such a processing device may be a microprocessor, micro-controller, digital signal processor, microcomputer, central processing unit, field programmable gate array, programmable logic device, state machine, logic circuitry, digital circuitry, and/or any device that manipulates signals based on operational instructions. The memory may be a single memory device or a plurality of memory devices. Such a memory device may be a read-only memory, random access memory, volatile memory, non-volatile memory, static memory, dynamic memory, flash memory, and/or any device that stores digital information. Note that when the processing device implements one or more of its functions via a state machine, digital circuitry, and/or logic circuitry, the memory storing the corresponding operational instructions is embedded with the circuitry comprising the state machine, digital circuitry, and/or logic circuitry.

Figure 3:
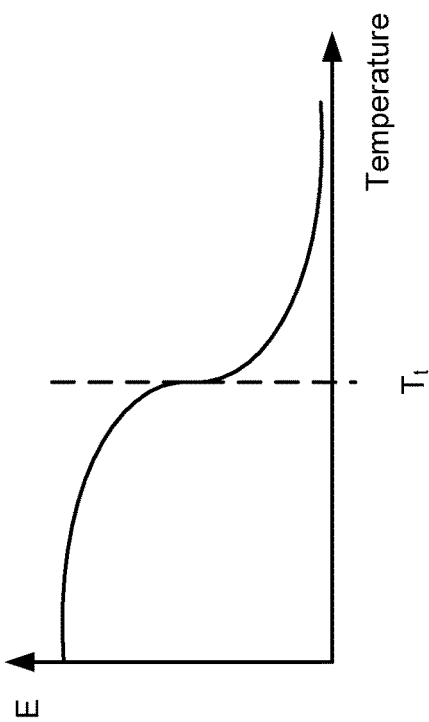
FIG. 3 is a graphical representation of a temperature profile of in accordance with an embodiment the present invention.

FIG. 3 is a graphical representation of a temperature profile in accordance with an embodiment of the present invention. In particular, a temperature profile is presented of a shape memory member, such as shape memory member 100. The shape memory member can be a shape memory polymer such as a cold hibernated elastic memory (CHEM) polymer or other shape memory polymer, shape memory alloy or other shape memory device. As shown, the elastic modulus, E, of the shape memory member 100 changes based on whether the temperature, T, of the shape memory member is above or below a transition temperature, $T_t$. For the range of temperatures $T<T_t$, the elastic modulus is high and the shape memory member is rigid and holds a particular shape. For the range of temperatures $T>T_t$, the elastic modulus is low and the shape memory member is flexible. Consider the example where the shape memory member 100 is a shape memory polymer that has a transition temperature, $T_t$, that corresponds to a glass transition. For the range of temperatures $T<T_t$, the shape memory member is in a glassy state and is rigid. For the range of temperatures $T>T_t$, the shape memory member is in a rubbery state and the shape memory member is flexible. This property of the shape memory member can be used to create a heat induced shape transformation as described in conjunction with FIG. 4.

FIG. 4 is a flow diagram of an embodiment of a method in accordance with the present invention. In step 120, a shape memory member, such as shape memory member 100 of shape memory catheterization device 98, is heated above its transition temperature and enters a flexible state. In step 122, the shape memory member is deformed from an original shape into its catheterization shape. In step 124, the shape memory member is cooled while constrained to its catheterization shape, and becomes rigid, allowing it to retain its deformed catheterization shape when the constraint is removed. In step 126, the shape memory member is heated during catheterization for deployment as part of the catheterization treatment. When the shape memory member reenters the rubbery state, the shape memory member undergoes a shape transformation back to its original shape.

As shown in step 128, the shape transformation of the shape memory member 100 is detected based on transformation data, such as transformation data 106 generated by the transformation data generator 104. As discussed in conjunction with FIG. 1, the transformation data 106 can be displayed or otherwise used to provide visual, audible or tactile feedback to the users of shape memory catheterization device 98 that the shape memory member 100 has reached its transformation shape. As discussed in conjunction with FIG. 2, the transformation data can be used by a heating control generator to generate the control signal 108 to discontinue the heating of the shape memory member 100 when the transformation data indicates the shape transformation of the shape memory member has gone from the catheterization shape to the transformed shape. If the shape memory member 100 is a stent or other device that is to remain in the body, the cooling of the shape memory member back to the body temperature of the patient causes the shape memory member to return to its rigid state to hold the transformed shape.

Figure 5:
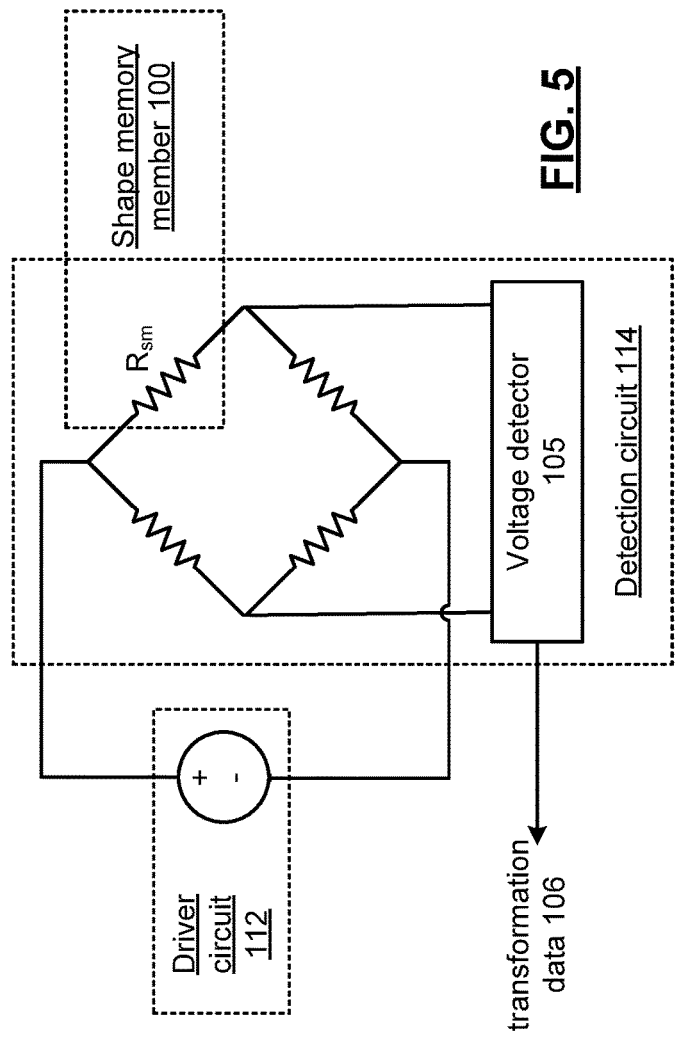
FIG. 5 is a schematic block diagram of an embodiment of a driver circuit 112 and detection circuit 114 in accordance with the present invention.

FIG. 5 is a schematic block diagram of an embodiment of a driver circuit 112 and detection circuit 114 in accordance with the present invention. In this embodiment, the shape memory member 100 includes a resistive element that has a resistance $R_{sm}$ that changes in response to the shape transformation of the shape memory member. For example, the shape memory member 100 can be a shape memory polymer with electrically resistive properties, that is surface doped with a conductive or partially conductive compound, or that is doped to saturation with a conductive or partially conductive compound. In a further example the shape memory member can be formed of a shape memory polymer to include a flexible resistive member such as a metallic foil element adhered or deposited on the surface of the shape memory member, a flexible foil or coil insert, a resistive foam member or insert or other resistive member. In addition, the shape memory member can be formed of a shape memory alloy that is electrically conductive with a resistance that changes in response to the shape transformation of the shape memory member 100.

The driver circuit includes a power source, such as the voltage source shown, that drives the detection circuit 114 and a wheatstone bridge formed with the resistive element of the shape memory member 100 and a plurality of fixed resistors. The voltage detector 105 monitors the change in resistance of the resistive element of shape memory member 100 and generates the transformation data 104, for example, when the change in resistance $R_{sm}$ indicates that the shape transformation has occurred.

In an embodiment, the voltage detector 105 generates the transformation data 106 to indicate the shape transformation of the shape memory member from the catheterization shape to the transformed shape when the resistance $R_{sm}$ of the resistive element compares favorably to a transformation threshold. In particular, the transformation data 106 can include a data flag having a first value that indicates the catheterization shape and a second value that indicates the transformed shape. The transition of the transformation data 106 from the first value to the second value can indicate that the transformation has occurred.

Figure 6:
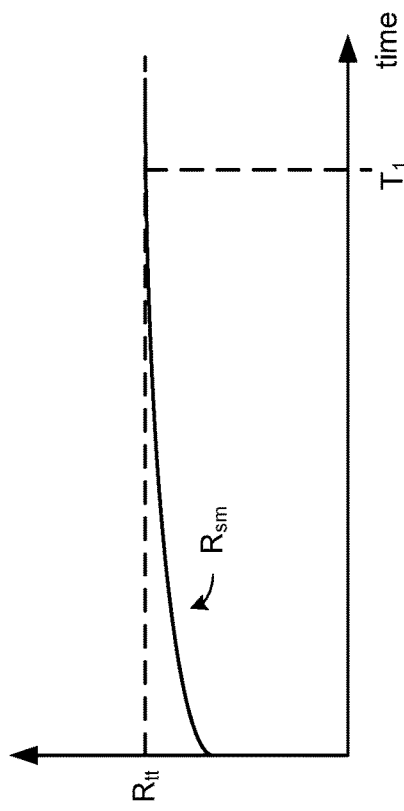
FIG. 6 is a graphical representation of a resistance profile of in accordance with an embodiment the present invention.

FIG. 6 is a graphical representation of a resistance profile of in accordance with an embodiment the present invention. An example resistance profile of a resistive element of shape memory member 100 is shown. As the shape memory member is heated in conjunction with the deployment of the shape memory catheterization device, the resistance, $R_{sm}$, changes with time. In particular, the resistance $R_{sm}$ changes in response to the shape transformation of the shape memory member 100 caused by the heating of the shape memory catheterization device.

As discussed in conjunction with FIG. 5, the voltage detector 105 generates the transformation data 106 to indicate the shape transformation of the shape memory member 100 from the catheterization shape to the transformed shape when the resistance $R_{sm}$ of the resistive element compares favorably to a transformation threshold. In the example shown, the transformation over time of the shape memory member causes the resistance $R_{sm}$ to increase. At a time, $T_1$, the resistance $R_{sm}$ reaches a transition threshold, $R_{tt}$, and stabilizes indicating the shape transformation is complete. In this example the voltage detector can include a comparator that generates the transformation data 106 when the $R_{sm}$ meets or exceeds the transition threshold, $R_{tt}$.

While the transformation over time of the shape memory member causes the resistance $R_{sm}$ to increase in the example shown, in other examples, the resistance may decrease depending on the nature of the original and catheterization shape of the shape memory member and/or the nature, position and orientation of the resistive element or elements included in the shape memory member 100, etc. Further, while the voltage detector has been described in terms of comparing the resistance $R_{sm}$ to a transition threshold, $R_{tt}$. Other metrics such as the stabilization of the resistance $R_{sm}$ can likewise be employed.

Further, while the embodiments above contemplate a shape memory device 100 with a single resistive element, multiple resistive elements can be driven and monitored by transformation data generator 102. For example, resistive elements can be placed at multiple points, on multiple axes of transformation or otherwise on multiple portions of a shape memory member 100. In this configuration, transformation data 106 can be generated to indicate the transform shape when all of the resistive elements indicate a transformation has taken place.

Figure 7:
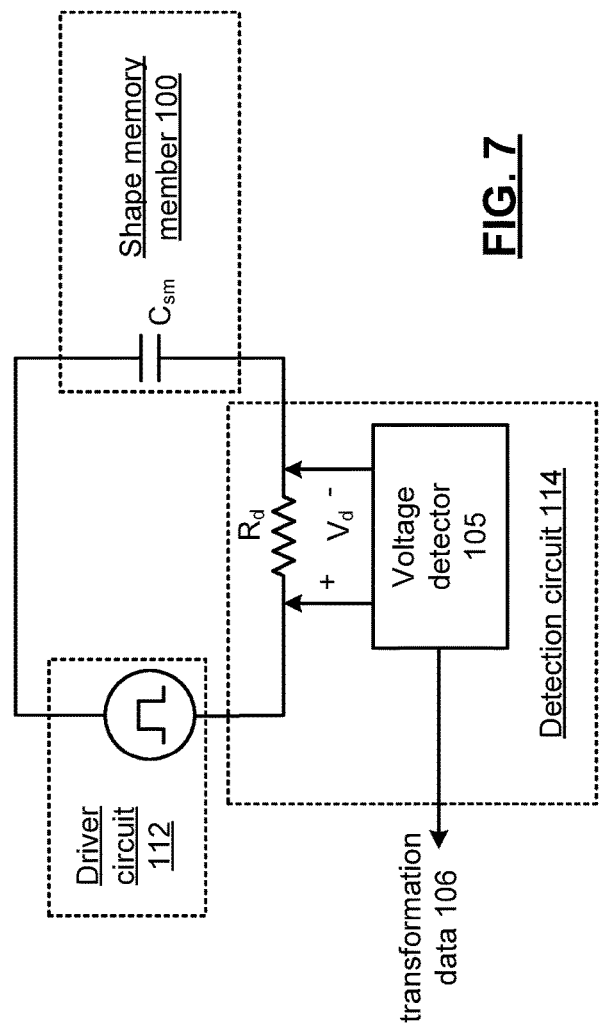
FIG. 7 is a schematic block diagram of an embodiment of a driver circuit 112 and detection circuit 114 in accordance with the present invention.

FIG. 7 is a schematic block diagram of an embodiment of a driver circuit 112 and detection circuit 114 in accordance with the present invention. In this embodiment, the shape memory member 100 includes a capacitive element that has a capacitance $C_{sm}$ that changes in response to the shape transformation of the shape memory member. For example, the shape memory member 100 can be a shape memory polymer with capacitive properties, that is includes a plurality of plates that are surface doped with a conductive or partially conductive compound, a metallic foil element adhered or deposited on the surface of the shape memory member or a conductive foam or other conductive element that forms the plates. The shape memory polymer further includes an electrolytic, dielectric or insulator made of a shape memory polymer that is disposed between the plurality of plates. In addition, the shape memory member can be formed of a shape memory alloy that is electrically conductive with a capacitance such as a parasitic capacitance that changes in response to the shape transformation of the shape memory member 100.

The driver circuit 112 includes a power source, such as the voltage source shown, that drives the detection circuit 114 via an alternating current such as the step waveform generator that is shown. The driver circuit further includes a detection resistance $R_d$ that forms an RC circuit with the capacitive element of the shape memory member 100. The voltage detector 105 monitors the change in capacitance of the capacitive element of shape memory member 100 based on monitoring the time of charging and/or discharging of the capacitive element. The voltage detector generates the transformation data 104, for example, when the change in capacitance $C_{sm}$ indicates that the shape transformation has occurred.

In an embodiment, the voltage detector 105 generates the transformation data 106 to indicate the shape transformation of the shape memory member from the catheterization shape to the transformed shape when the capacitance $C_{sm}$ of the capacitive element compares favorably to a transformation threshold. In particular, the transformation data 106 can include a data flag having a first value that indicates the catheterization shape and a second value that indicates the transformed shape. The transition of the transformation data 106 from the first value to the second value can indicate that the transformation has occurred.

Figure 8:
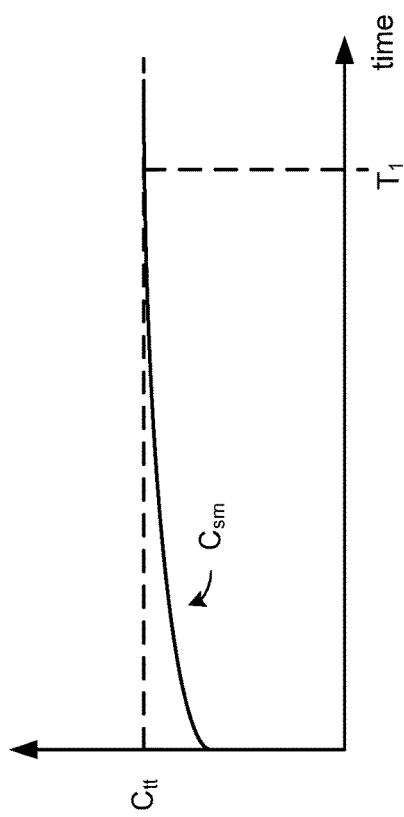
FIG. 8 is a graphical representation of a capacitance profile of in accordance with an embodiment the present invention.

FIG. 8 is a graphical representation of a capacitance profile of in accordance with an embodiment the present invention. An example capacitance profile of a capacitive element of shape memory member 100 is shown. As the shape memory member 100 is heated in conjunction with the deployment of the shape memory catheterization device, the capacitance, $C_{sm}$, changes with time. In particular, the capacitance $C_{sm}$ changes in response to the shape transformation of the shape memory member caused by the heating of the shape memory catheterization device.

As discussed in conjunction with FIG. 7, the voltage detector 105 generates the transformation data 106 to indicate the shape transformation of the shape memory member from the catheterization shape to the transformed shape when the capacitance $C_{sm}$ of the capacitive element compares favorably to a transformation threshold. In the example shown, the transformation over time of the shape memory member causes the capacitance $C_{sm}$ to increase. At a time, $T_1$, the capacitance $C_{sm}$ reaches a transition threshold, $C_{tt}$, and stabilizes indicating the shape transformation is complete. In this example the voltage detector can include a comparator that generates the transformation data 106 when the $C_{sm}$ meets or exceeds the transition threshold, $C_{tt}$.

While the transformation over time of the shape memory member causes the capacitance $C_{sm}$ to increase in the example shown, in other examples, the capacitance may decrease depending on the nature of the original and catheterization shape of the shape memory member and/or the nature, position and orientation of the capacitive element or elements included in the shape memory member, etc. Further, while the voltage detector has been described in terms of comparing the capacitance $C_{sm}$ to a transition threshold, $C_{tt}$. Other metrics such as the stabilization of the capacitance $C_{sm}$ can likewise be employed.

Further, while the embodiments above contemplate a shape memory device with a single capacitive element, multiple capacitive elements can be driven and monitored by transformation data generator 102. For example, capacitive elements can be placed at multiple points, on multiple axes of transformation or otherwise on multiple portions of a shape memory member 100. In this configuration, transformation data 106 can be generated to indicate the transformation shape when all of the capacitive elements indicate a transformation has taken place.

Figure 9:
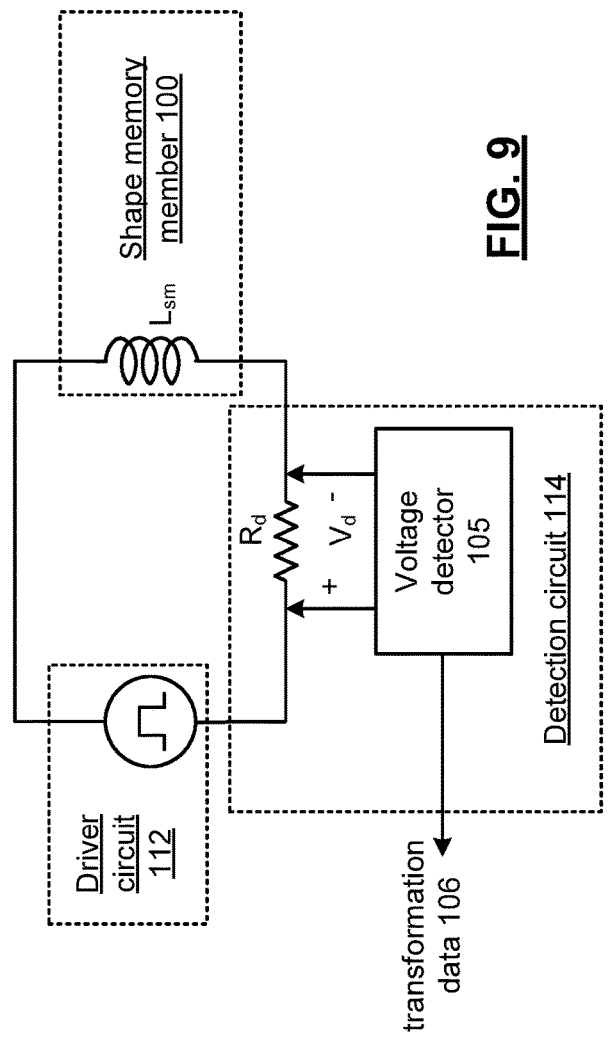
FIG. 9 is a schematic block diagram of an embodiment of a driver circuit 112 and detection circuit 114 in accordance with the present invention.

FIG. 9 is a schematic block diagram of an embodiment of a driver circuit 112 and detection circuit 114 in accordance with the present invention. In this embodiment, the shape memory member 100 includes an inductive element that has an inductance $L_{sm}$ that changes in response to the shape transformation of the shape memory member. For example, the shape memory member can be a shape memory polymer with electrically inductive properties, that is surface doped with a conductive or partially conductive compound, or that is doped to saturation with a conductive or partially conductive compound. In a further example the shape memory member can be formed of a shape memory polymer to include a flexible inductive member such as a metallic foil element adhered or deposited on the surface of the shape memory member, a flexible foil or coil insert, a conductive foam member or insert or other inductive member. In addition, the shape memory member can be formed of a shape memory alloy that is electrically conductive with an inductance that changes in response to the shape transformation of the shape memory member 100.

The driver circuit 112 includes a power source, such as the voltage source shown, that drives the detection circuit 114 via an alternating current such as the step waveform generator that is shown. The driver circuit further includes a detection resistance $R_d$ that forms an RL circuit with the inductive element of the shape memory member 100. The voltage detector 105 monitors the change in inductance of the inductive element of shape memory member 100 based on monitoring the time of charging and/or discharging of the inductive element. The voltage detector generates the transformation data 104, for example, when the change in inductance $L_{sm}$ indicates that the shape transformation has occurred.

In an embodiment, the voltage detector 105 generates the transformation data 106 to indicate the shape transformation of the shape memory member from the catheterization shape to the transformed shape when the inductance $L_{sm}$ of the inductive element compares favorably to a transformation threshold. In particular, the transformation data 106 can include a data flag having a first value that indicates the catheterization shape and a second value that indicates the transformed shape. The transition of the transformation data from the first value to the second value can indicate that the transformation has occurred.

Figure 10:
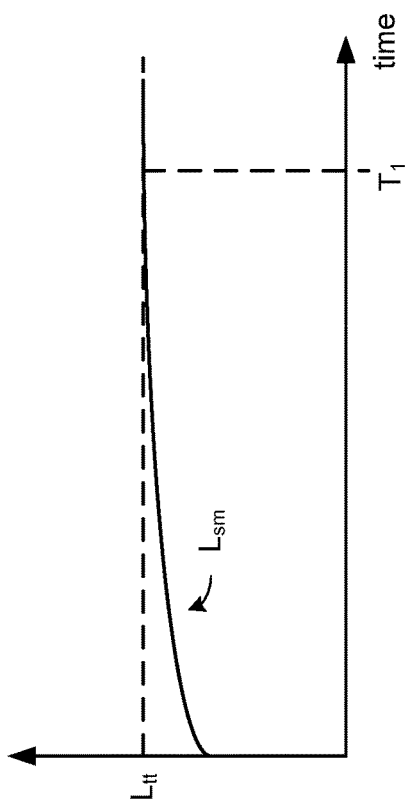
FIG. 10 is a graphical representation of inductance profile of in accordance with an embodiment the present invention.

FIG. 10 is a graphical representation of an inductance profile of in accordance with an embodiment the present invention. An example inductance profile of a inductive element of shape memory member 100 is shown. As the shape memory member is heated in conjunction with the deployment of the shape memory catheterization device, the inductance, $L_{sm}$, changes with time. In particular, the inductance $L_{sm}$ changes in response to the shape transformation of the shape memory member caused by the heating of the shape memory catheterization device.

As discussed in conjunction with FIG. 9, the voltage detector 105 generates the transformation data 106 to indicate the shape transformation of the shape memory member from the catheterization shape to the transformed shape when the inductance $L_{sm}$ of the inductive element compares favorably to a transformation threshold. In the example shown, the transformation over time of the shape memory member causes the inductance $L_{sm}$ to increase. At a time, $T_1$, the inductance $L_{sm}$ reaches a transition threshold, $L_{tt}$, and stabilizes indicating the shape transformation is complete. In this example the voltage detector can include a comparator that generates the transformation data 106 when the inductance $L_{sm}$ meets or exceeds the transition threshold, $L_{tt}$.

While the transformation over time of the shape memory member causes the inductance $L_{sm}$ to increase in the example shown, in other examples, the inductance may decrease depending on the nature of the original and catheterization shape of the shape memory member and/or the nature, position and orientation of the inductive element or elements included in the shape memory member, etc. Further, while the voltage detector has been described in terms of comparing the inductance $L_{sm}$ to a transition threshold, $L_{tt}$. Other metrics such as the stabilization of the inductance $L_{sm}$ can likewise be employed.

Further, while the embodiments above contemplate a shape memory device with a single inductive element, multiple inductive elements can be driven and monitored by transformation data generator 102. For example inductive elements can be placed at multiple points, on multiple axes of transformation or otherwise on multiple portions of a shape memory member 100. In this configuration, transformation data 106 can be generated to indicate the transform shape when all of the inductive elements indicate a transformation has taken place.

Figure 11:
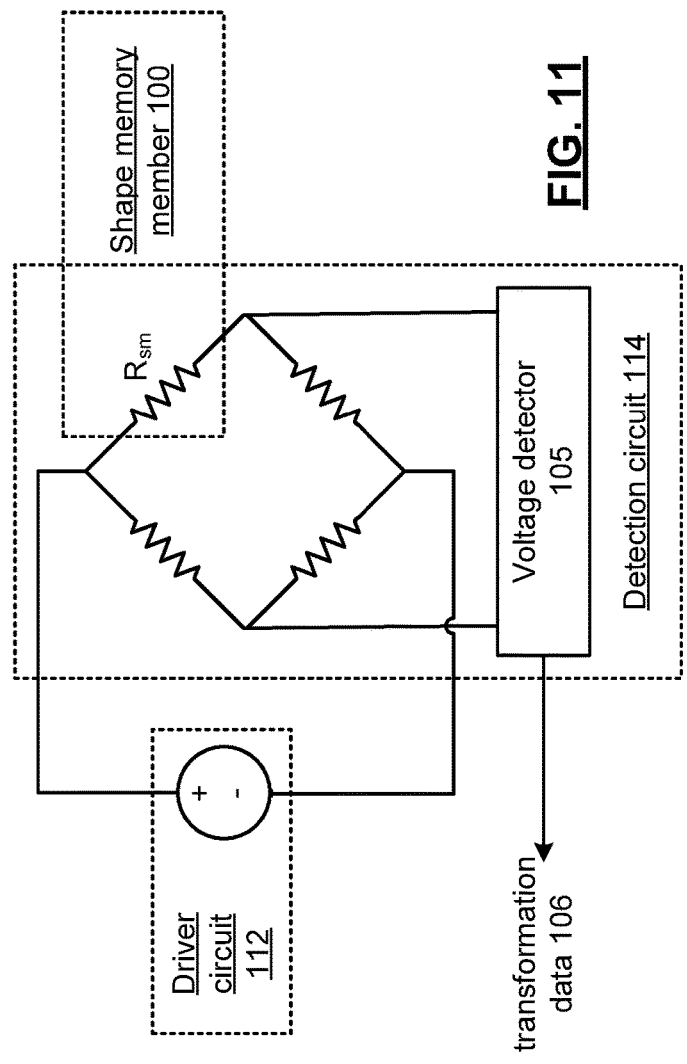
FIG. 11 is a schematic block diagram of an embodiment of a driver circuit 112 and detection circuit 114 in accordance with the present invention.

FIG. 11 is a schematic block diagram of an embodiment of a driver circuit 112 and detection circuit 114 in accordance with the present invention. In this embodiment, the shape memory member 100 includes a strain gage that has a resistance $R_{sm}$ that changes in response to strain on the shape memory member 100. For example, the shape memory member 100 can be a shape memory polymer or other shape memory member with a strain gage adhered or deposited on the surface of the shape memory member. In particular, strain and corresponding resistance $R_{sm}$ change with the shape transformation of the shape memory member 100.

The driver circuit includes a power source, such as the voltage source shown, that drives the detection circuit 114, and a wheatstone bridge formed with the resistive element $R_{sm}$ of the strain gage of shape memory member 100 and a plurality of fixed resistors. The voltage detector 105 monitors the change in strain of the strain gage by monitoring the resistance of strain gage and generates the transformation data 104, for example, when the change in resistance $R_{sm}$ indicates that the shape transformation has occurred.

In an embodiment, the voltage detector 105 generates the transformation data 106 to indicate the shape transformation of the shape memory member from the catheterization shape to the transformed shape when the resistance $R_{sm}$ (corresponding to the strain of the strain gage) compares favorably to a transformation threshold. In particular, the transformation data 106 can include a data flag having a first value that indicates the catheterization shape and a second value that indicates the transformed shape. The transition of the transformation data from the first value to the second value can indicate that the transformation has occurred.

Figure 12:
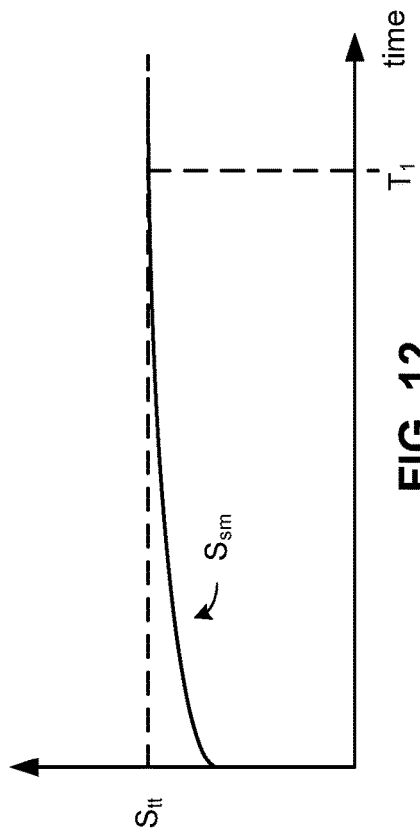
FIG. 12 is a graphical representation of a strain profile of in accordance with an embodiment the present invention.

FIG. 12 is a graphical representation of a strain profile of in accordance with an embodiment the present invention. An example strain profile of a strain gage of shape memory member 100 is shown. As the shape memory member is heated in conjunction with the deployment of the shape memory catheterization device, the strain, $S_{sm}$, changes with time. In particular, the strain $S_{sm}$ changes in response to the shape transformation of the shape memory member caused by the heating of the shape memory catheterization device.

As discussed in conjunction with FIG. 11, the voltage detector 105 generates the transformation data 106 to indicate the shape transformation of the shape memory member from the catheterization shape to the transformed shape when the resistance $R_{sm}$ corresponding to the strain $S_{sm}$ of the strain gage compares favorably to a transformation threshold. In the example shown, the transformation over time of the shape memory member causes the strain $S_{sm}$ to increase. At a time, $T_1$, the strain $S_{sm}$ reaches a transition threshold, $S_{tt}$, and stabilizes indicating the shape transformation is complete. In this example the voltage detector can include a comparator that generates the transformation data 106 when the $S_{sm}$ meets or exceeds the transition threshold, $S_{tt}$.

While the transformation over time of the shape memory member causes the strain $S_{sm}$ to increase in the example shown, in other examples, the strain may decrease depending on the nature of the original and catheterization shape of the shape memory member and/or the nature, position and orientation of the strain gage or gages included in the shape memory member, etc. Further, while the voltage detector has been described in terms of comparing the strain $S_{sm}$ to a transition threshold, $S_{tt}$. Other metrics such as the stabilization of the strain $S_{sm}$ can likewise be employed.

Further, while the embodiments above contemplate a shape memory device with a single strain gage, multiple strain gages can be driven and monitored by transformation data generator 102. For example, strain gages can be placed at multiple points, on multiple axes of transformation or otherwise on multiple portions of a shape memory member 100. In this configuration, transformation data 106 can be generated to indicate the transform shape when all of the strain gages indicate a transformation has taken place.

Figure 13:
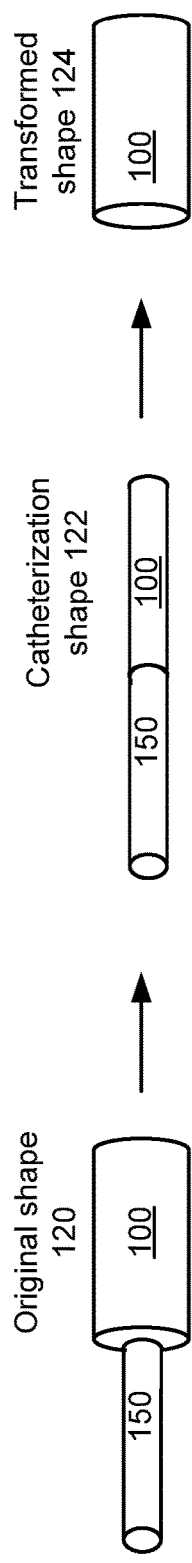
FIG. 13 is a pictorial representation of the shape transformation of a shape memory member of in accordance with an embodiment the present invention.

FIG. 13 is a pictorial representation of the shape transformation of a shape memory member of in accordance with an embodiment the present invention. In particular, a shape memory member 100 is presented as a cylinder. Examples of such shape memory members include a cylindrical tube constructed with shape memory polymer for grafting a vein or artery to treat an aneurism or a cylindrical tube constructed with shape memory polymer or cylindrical mesh constructed with either a shape memory polymer or shape memory alloy for supporting a vein or artery after removing a blockage. In the configuration shown, the shape memory member 100 is fitted on a delivery rod to be delivered through a delivery rod 150 (a portion of which is shown schematically) and is deformed from an original shape 120 into a catheterization shape 122 with reduced diameter via crimping. When the shape memory member 100 is heated during deployment, it transforms into the transformed shape 124 that is substantially the original shape 120, subject to, for example, physical conformity to the tissue, such as the vein, artery or other tissue in which the shape memory catheterization device is deployed.

While the catheterization shape 122 is shown as cylindrical, other shapes are possible including a flattened cylinder, and other shapes, based on the particular method of deformation and further based on the desired shape for catheterization. Further, while the original shape 120 is shown as cylindrical, other regular geometrical shapes such as spherical, pyramidal, etc. could likewise be employed as well as any number of irregular shapes, based on the desired shape for deployment of the shape memory member 100.

It should be noted that the shape memory member 100 can be detached from the delivery rod 150 after being placed in the proper tissue location for deployment and left in the patient. In embodiments where the shape memory member 100 includes a shape memory polymer, the shape memory polymer can be doped with a drug, such as an anticoagulant to reducing clotting, a drug to promote acceptance of the device by the surrounding tissue or other drug.

Figure 14:
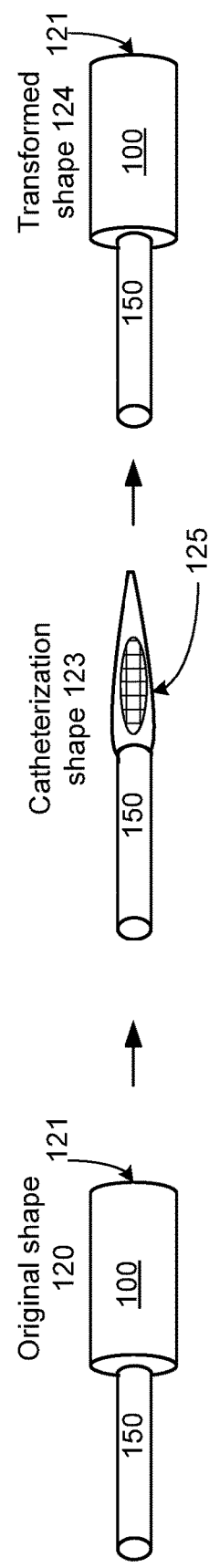
FIG. 14 is a pictorial representation of the transformation of a shape memory member of in accordance with an embodiment the present invention.

FIG. 14 is a pictorial representation of the transformation of a shape memory member of in accordance with an embodiment the present invention. In particular, a shape memory member 100 is presented as a cylinder. Examples of such shape memory members include a cylindrical cup for holding a drug for intravenous deployment. In the configuration shown, the closed end of the cup is fitted to a delivery rod 150, (the end of which is shown schematically) and the inner portion of the cup is packed with the drug to be deployed via the open end 121 and is then deformed from an original shape 120 into a catheterization shape 123 via crimping. As shown the open end 121 of the original shape 120 is closed in the catheterization shape 123 to hold the drug for catheterization in a pocket 125 for deployment. When the shape memory member 100 is heated during deployment, it transforms into transformed shape 124 that is substantially the original shape 120, subject to, for example, physical conformity to the tissue, such as the vein, artery or other tissue in which the shape memory device is deployed. The end 121 of the cup opens for release of the drug.

While the catheterization shape 122 is shown as cylindrical, other shapes are possible including a flattened cylinder, and other shapes, based on the particular method of deformation and further based on the desired shape for catheterization. Further, while the original shape 120 is shown as cylindrical, other regular geometrical shapes such as spherical, pyramidal, etc. could likewise be employed as well as any number of irregular shapes, based on the desired shape for deployment of the shape memory member.

It should be noted that the shape memory member 100 can remain attached to the delivery rod 150 after being placed in the proper tissue location for deployment and removed from the patient after the drug is released. In embodiments where the shape memory member includes a shape memory polymer, the shape memory polymer can also be doped with a drug, such as an anticoagulant to reducing clotting, or other drug.

Figure 15:
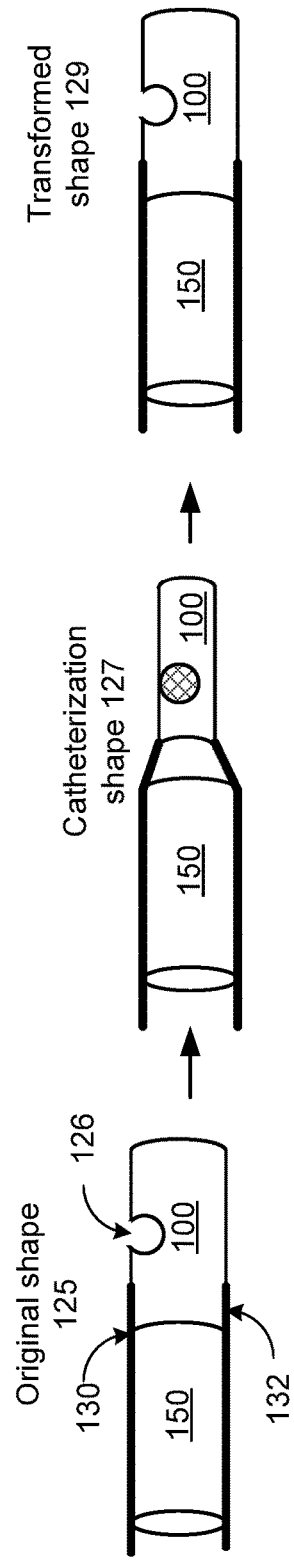
FIG. 15 is a pictorial representation of the transformation of a shape memory member of in accordance with an embodiment the present invention.

FIG. 15 is a pictorial representation of the transformation of a shape memory member of in accordance with an embodiment the present invention. In particular, a shape memory member 100 is presented as a cylinder. Examples of such shape memory members include a cylindrical with a spherical pocket 126 for holding a drug for intravenous deployment. In the configuration shown, the cylinder is fitted to a delivery rod 150, (the end of which is shown schematically) and the pocket 126 is packed with the drug to be deployed and is then deformed from an original shape 125 into a catheterization shape 127 via crimping a portion of the cylinder shown. As shown, the pocket 126 of the original shape 125 is closed in the catheterization shape 127 to hold the drug for catheterization in a pocket 126 for deployment. When the shape memory member 100 is heated during deployment, it transforms into transformed shape 129 that is substantially the original shape 125, subject to, for example, physical conformity to the tissue, such as the vein, artery or other tissue in which the shape memory device is deployed. The pocket 126 opens for release of the drug.

While the catheterization shape 127 is shown as cylindrical, other shapes are possible including a flattened cylinder, and other shapes, based on the particular method of deformation and further based on the desired shape for catheterization. Further, while the original shape 125 is shown as cylindrical, other regular geometrical shapes such as a spherical, pyramidal, etc. could likewise be employed as well as any number of irregular shapes, based on the desired shape for deployment of the shape memory member. In a further embodiment, the shape memory member can be a hollow cup that is crimped to hold the ball end of a medical device and that releases the ball end for deployment. Further, while a single pocket 126 is shown, a shape memory member 100 with multiple pockets could be implemented in a similar fashion.

It should be noted that the shape memory member 100 can remain attached to the delivery rod 150 after being placed in the proper tissue location for deployment and removed from the patient after the drug is released. Delivery rod 150 includes a plurality of electrodes 130 and 132 that electrically couple to the shape memory member 100. In operation, the electrodes couple a transformation data generator 110 to a capacitive, resistive element or an inductive element of shape memory member 100 or a strain gage coupled thereto. The plurality of electrodes are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

In embodiments where the shape memory member 100 includes a shape memory polymer, the shape memory polymer can also be doped with a drug, such as an anticoagulant to reducing clotting, or other drug. While a particular medical device is shown, other medical devices can similarly deployed. Further, while the medical device is shown with a ball end, other catch designs including a pyramidal catch, a box catch or other shapes can likewise be implemented FIG. 16 is a pictorial representation of the transformation of a shape memory member of in accordance with an embodiment the present invention. In particular, a shape memory member 100 is shown along with electrodes 130 and 132 that electrically couple to the shape memory member. The electrodes can be part of a delivery rod such as delivery rod 150, not specifically shown.

In various embodiments, the shape memory member 100 can be detached from the delivery rod 150 after being placed in the proper tissue location for deployment and left in the patient. In these embodiments, the plurality of electrodes 130 and 132 decouple from the shape memory member 100 when the shape memory member 100 is detached from the delivery rod 150. In embodiments where the shape memory member 100 remains attached to the delivery rod and is removed from the patient's body after treatment the electrodes 130 and 132 can be more permanently attached to the shape memory member 100.

In operation, the electrodes couple a transformation data generator 110 to a resistive element or an inductive element of shape memory member 100. As previously discussed, the shape memory member can be a shape memory polymer with electrically resistive or inductive properties, that is surface doped with a conductive or partially conductive compound, or that is doped to saturation with a conductive or partially conductive compound. In a further example the shape memory member can be formed of a shape memory polymer to include a flexible resistive or inductive member such as a metallic foil element adhered or deposited on the surface of the shape memory member, a flexible foil or coil insert, a resistive foam member or insert or other resistive or inductive member. In addition, the shape memory member can be formed of a shape memory alloy that is electrically conductive with either a resistance or inductance that changes in response to the shape transformation of the shape memory member 100.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

FIG. 17 is a pictorial representation of the transformation of a shape memory member of in accordance with an embodiment the present invention. As in the embodiment of FIG. 16, a shape memory member 100 is shown along with electrodes 130 and 132 that electrically couple to the shape memory member. In this embodiment, the electrodes couple a transformation data generator 110 to a capacitive element of shape memory member 100 via conductive plates 134 and 136. The plates 134 and 136 can be constructed of metallic foil elements adhered or deposited on the surface of the shape memory member, conductive foam members or inserts or other conductive member. The shape memory element 100 can be doped with an electrolytic compound to increase the capacitance of the device.

FIG. 18 is a pictorial representation of the transformation of a shape memory member of in accordance with an embodiment the present invention. As in the embodiment of FIGS. 16 and 17, a shape memory member 100 is shown along with electrodes 130 and 132 that electrically couple to the shape memory member. In this embodiment, the electrodes couple a transformation data generator 110 to a strain gage 136 of shape memory member 100. The strain gage can be constructed of metallic foil elements adhered or deposited on the surface of the shape memory member, conductive foam members or inserts or other strain gage configurations.

FIG. 19 is a pictorial representation of the transformation of a shape memory member of in accordance with an embodiment the present invention. In particular, a shape memory member 100 is presented as a coil. Examples of such shape memory members include a coil constructed with shape memory alloy or shape memory polymer for to treat an aneurism by filling a weakened portion of a vein or artery. In the configuration shown, the shape memory member 100 is fitted on a catheter (not shown) and is deformed from an original shape 140 into a catheterization shape 142. When the shape memory member 100 is heated during deployment, it transforms into transformed shape 144 that is substantially the original shape 140, subject to, for example, physical conformity to the tissue, such as the vein, artery or other tissue in which the shape memory catheterization device is deployed.

The shape memory member 100 can be constructed of a resistive or conductive wire or other resistive or conductive material that is biocompatible. The shape transformation of the shape memory member 100 can be detected based on a change of resistance or inductance of the shape memory member.

It should be noted that the shape memory member 100 can be detached from the delivery rod 150 after being placed in the proper tissue location for deployment and left in the patient. In embodiments where the shape memory member includes a shape memory polymer, the shape memory polymer can be doped with a drug, such as an anticoagulant to reducing clotting, a drug to promote acceptance of the device by the surrounding tissue or other drug.

FIG. 20 is a pictorial representation of the transformation of a shape memory member of in accordance with an embodiment the present invention. In particular, a shape memory member 100 is presented as a cylinder. Examples of such shape memory members include a cylinder with a spherical pocket 126 for holding a medical device 146 such as a coil for intravenous deployment for treatment of an aneurism.

In the configuration shown, the shape memory member 100 is fitted to a delivery rod 150, (the end of which is shown schematically) and the pocket 126 is packed with a catch, such as a ball end of the medical device 146 to be deployed. The shape memory device 100 is then deformed from an original shape 145 into a catheterization shape 147 via crimping a portion of the cylinder shown. As shown, the pocket 146 of the original shape 145 is closed in the catheterization shape 147 to hold the ball end medical device for catheterization in the pocket 126 for deployment. When the shape memory member 100 is heated during deployment, it transforms into transformed shape 149 that is substantially the original shape 125, subject to, for example, physical conformity to the tissue, such as the vein, artery or other tissue in which the shape memory device is deployed. The pocket 126 opens for release of the medical device 146. In the embodiment shown, the medical device 146 is itself constructed of a shape memory member, such as a shape memory wire, alloy or polymer that is compressed into a catheterization shape and that expands to its own transformed shape for treatment.

While the catheterization shape 147 is shown as cylindrical, other shapes are possible including a flattened cylinder, and other shapes, based on the particular method of deformation and further based on the desired shape for catheterization. Further, while the original shape 145 is shown as cylindrical, other regular geometrical shapes such as spherical, pyramidal, etc. could likewise be employed as well as any number of irregular shapes, based on the desired shape for deployment of the shape memory member. Further, while a single pocket 146 is shown, a shape memory member 100 with multiple pockets could be implemented in a similar fashion.

It should be noted that the shape memory member 100 can remain attached to the delivery rod 150 after being placed in the proper tissue location for deployment and removed from the patient after the medical device 146 is released. Delivery rod 150 includes a plurality of electrodes 130 and 132 that electrically couple to the shape memory member 100. In operation, the electrodes couple a transformation data generator 110 to a capacitive, resistive element or an inductive element of shape memory member 100 or a strain gage coupled thereto. The plurality of electrodes are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

In embodiments where the shape memory member 100 includes a shape memory polymer, the shape memory polymer can also be doped with a drug, such as an anticoagulant to reducing clotting, or other drug.

FIGS. 21 and 22 present pictorial representations of a shape memory member and delivery rod in accordance with an embodiment the present invention. Like the embodiment of FIG. 19, a shape memory member 100 is presented as a coil such as a coil constructed with shape memory alloy or shape memory polymer for to treat an aneurism by filling a weakened portion of a vein or artery. In the configuration shown, the shape memory member 100 is fitted on a delivery rod 150 and is deformed from an original shape shown in FIG. 21 into a catheterization shape shown in FIG. 22. When the shape memory member 100 is heated during deployment, it transforms into transformed shape that is substantially the original shape, subject to, for example, physical conformity to the tissue, such as the vein, artery or other tissue in which the shape memory catheterization device is deployed.

It should be noted that the shape memory member 100 can be detached from the delivery rod 150 after being placed in the proper tissue location for deployment and left in the patient. Delivery rod 150 includes a plurality of electrodes 130 and 132 that electrically couple to the shape memory member 100 and that decouple from the shape memory member 100 when the shape memory member 100 is detached from the delivery rod 150. In operation, the electrodes couple a transformation data generator 110 to a capacitive, resistive element or an inductive element of shape memory member 100 or a strain gage coupled thereto. The plurality of electrodes 130 and 132 are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example, the plurality of electrodes 130 and 132 can be formed a flexible conductive foam member or insert or other conductive member. It should be noted that the shape memory member 100 can be detached from the delivery rod 150 and electrodes 130 and 132 after being placed in the proper tissue location for deployment and left in the patient.

FIG. 23 is a pictorial representation of a shape memory member and catheter in accordance with an embodiment the present invention. In particular, a cross section is shown of a cylindrical shape memory member 100 and electrodes 130 and 132. In this embodiment the electrodes are arc shaped to conform with the outer surface of the cylindrical shape memory member 100. While each electrode 130 or 132 is shown as a single homogeneous element, each electrode can include a central palm and a plurality of fingers each having a longitudinal axis along the longitudinal axis of the cylindrical shape memory member 100. In this configuration, the fingers of each electrode lend themselves to being crimped into a position of contact when the shape memory member 100 is deformed for catheterization and to remain in contact with the shape memory member 100 when the shape memory member 100 undergoes its shape transformation.

Figure 24:
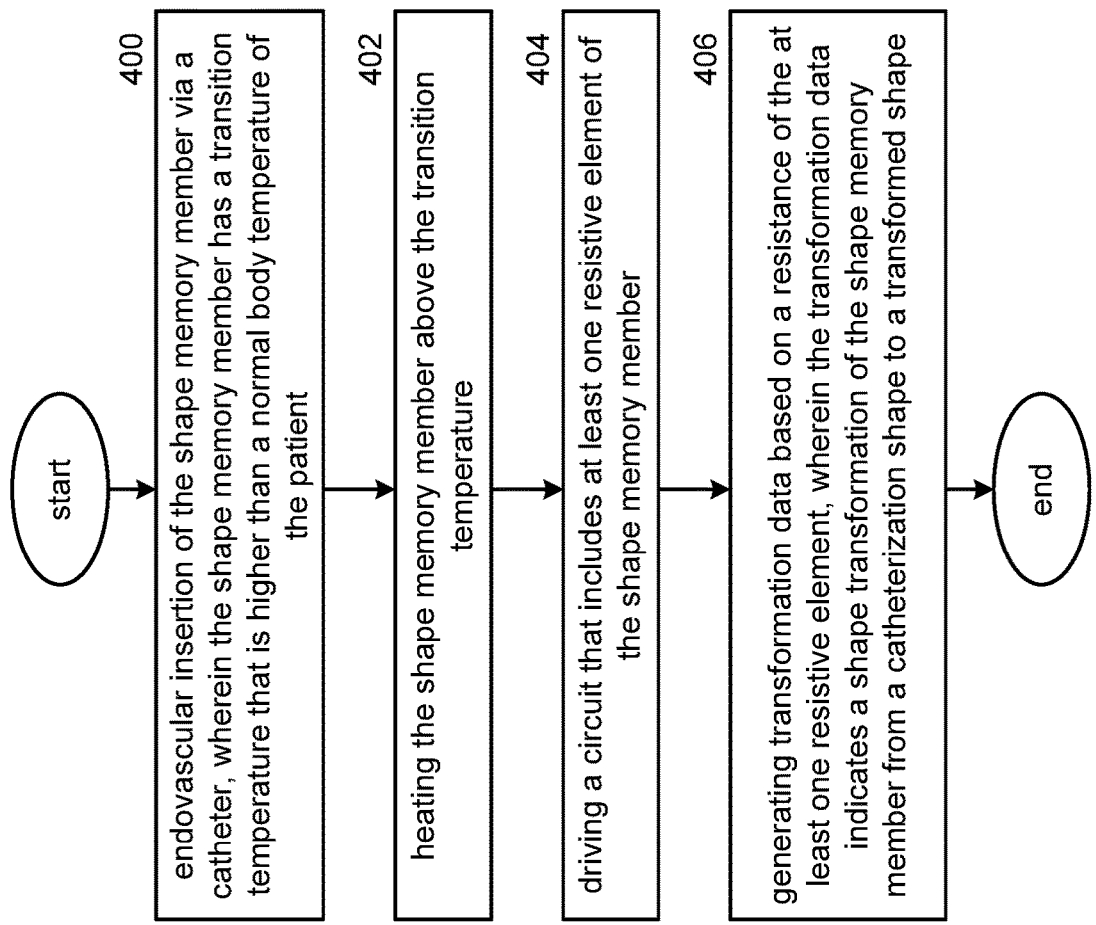
FIG. 24 is a flowchart representation of an embodiment of a method in accordance with the present invention.

FIG. 24 is a flowchart representation of an embodiment of a method in accordance with the present invention. In particular, a method is presented for use in conjunction with one or more features and functions described in conjunction with FIGS. 1-23. Step 400 includes endovascular insertion of the shape memory member via a catheter, wherein the shape memory member has a transition temperature that is higher than a normal body temperature of the patient. Step 402 includes heating the shape memory member above the transition temperature. Step 404 includes driving a circuit that includes at least one resistive element of the shape memory member. Step 406 includes generating transformation data based on a resistance of the at least one resistive element, wherein the transformation data indicates a shape transformation of the shape memory catheterization device from a catheterization shape to a transformed shape.

In an embodiment, the transformation data is generated to indicate the shape transformation of the shape memory member from the catheterization shape to the transformed shape when the resistance of the at least one resistive element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 25:
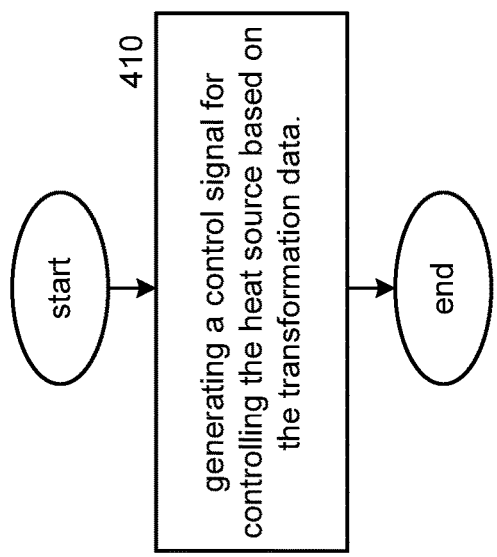
FIG. 25 is a flowchart representation of an embodiment of a method in accordance with the present invention.

FIG. 25 is a flowchart representation of an embodiment of a method in accordance with the present invention. In particular, a method is presented for use in conjunction with one or more features and functions described in conjunction with FIGS. 1-24. Step 410 includes generating a control signal for controlling the heat source based on the transformation data. In an embodiment, a control signal is generated to discontinue the heating of the shape memory member when the transformation data indicates the shape transformation of the shape memory member from the catheterization shape to the transformed shape.

Figure 26:
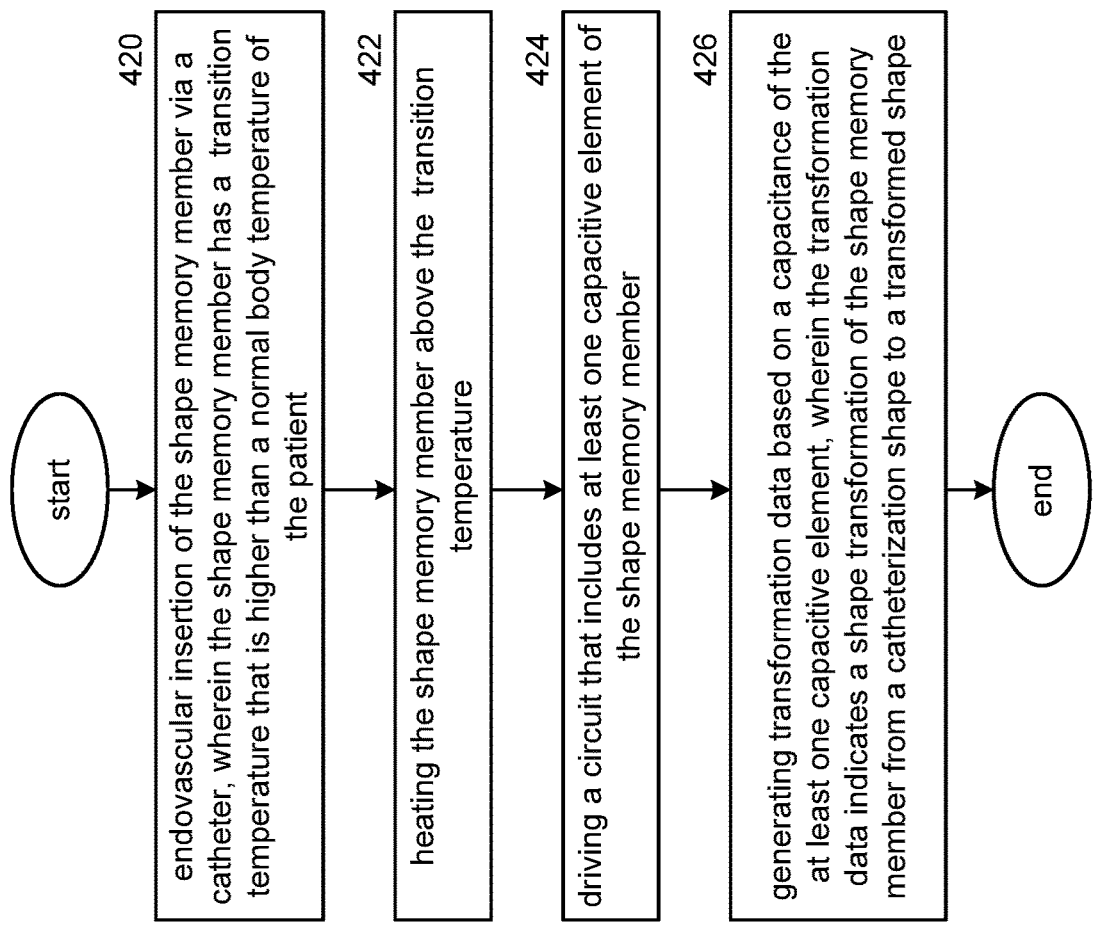
FIG. 26 is a flowchart representation of an embodiment of a method in accordance with the present invention.

FIG. 26 is a flowchart representation of an embodiment of a method in accordance with the present invention. In particular, a method is presented for use in conjunction with one or more features and functions described in conjunction with FIGS. 1-25. Step 420 includes endovascular insertion of the shape memory member via a delivery rod through a catheter, wherein the shape memory member has a transition temperature that is higher than a normal body temperature of the patient. Step 422 includes heating the shape memory member above the transition temperature. Step 424 includes driving a circuit that includes at least one capacitive element of the shape memory member. Step 426 includes generating transformation data based on a capacitance of the at least one capacitive element, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the capacitance of the at least one capacitive element compares favorably to a transformation threshold. The transformation data can include a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 27:
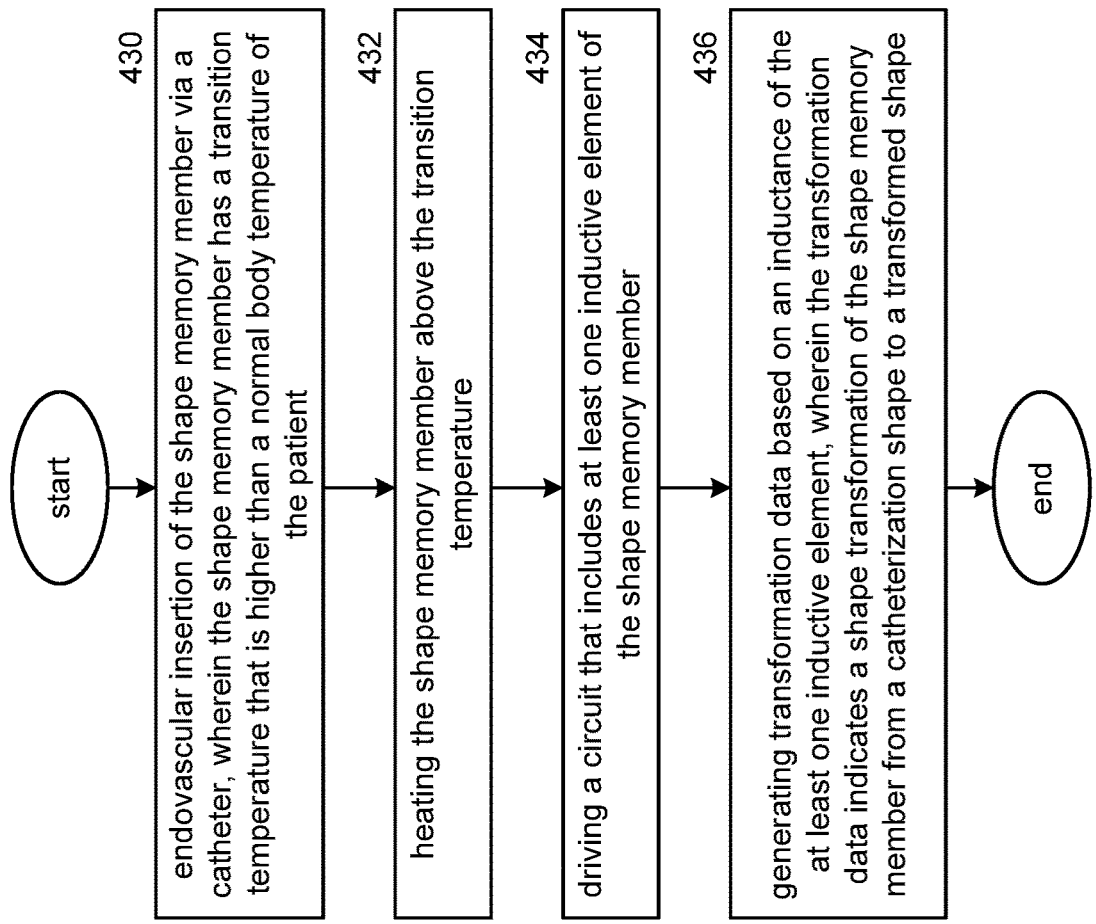
FIG. 27 is a flowchart representation of an embodiment of a method in accordance with the present invention.

FIG. 27 is a flowchart representation of an embodiment of a method in accordance with the present invention. In particular, a method is presented for use in conjunction with one or more features and functions described in conjunction with FIGS. 1-26. Step 430 includes endovascular insertion of a shape memory member via a delivery rod through a catheter, wherein the shape memory member has a transition temperature that is higher than a normal body temperature of the patient. Step 432 includes heating the shape memory member above the transition temperature. Step 434 includes driving a circuit that includes at least one inductive element of the shape memory member. Step 436 includes generating transformation data based on an inductance of the at least one inductive element, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the inductance of the at least one inductive element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 28:
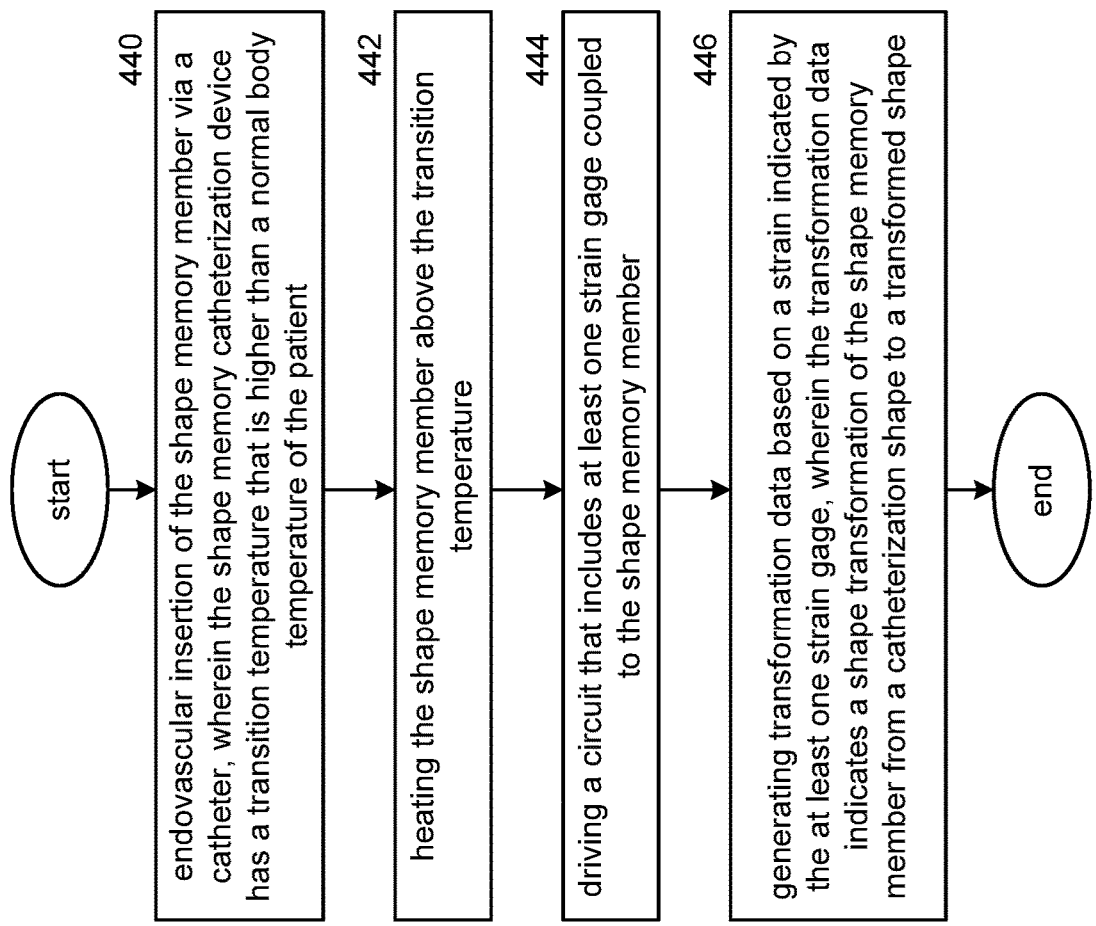
FIG. 28 is a flowchart representation of an embodiment of a method in accordance with the present invention.

FIG. 28 is a flowchart representation of an embodiment of a method in accordance with the present invention. In particular, a method is presented for use in conjunction with one or more features and functions described in conjunction with FIGS. 1-27. Step 440 includes endovascular insertion of the shape memory member via a delivery rod through a catheter, wherein the shape memory member has a transition temperature that is higher than a normal body temperature of the patient. Step 442 includes heating the shape memory member above the transition temperature. Step 444 includes driving a circuit that includes at least one strain gage coupled to the shape memory member. Step 446 includes generating transformation data based on a strain indicated by the at least one strain gage, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the strain indicated by the at least one strain gage element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 29:
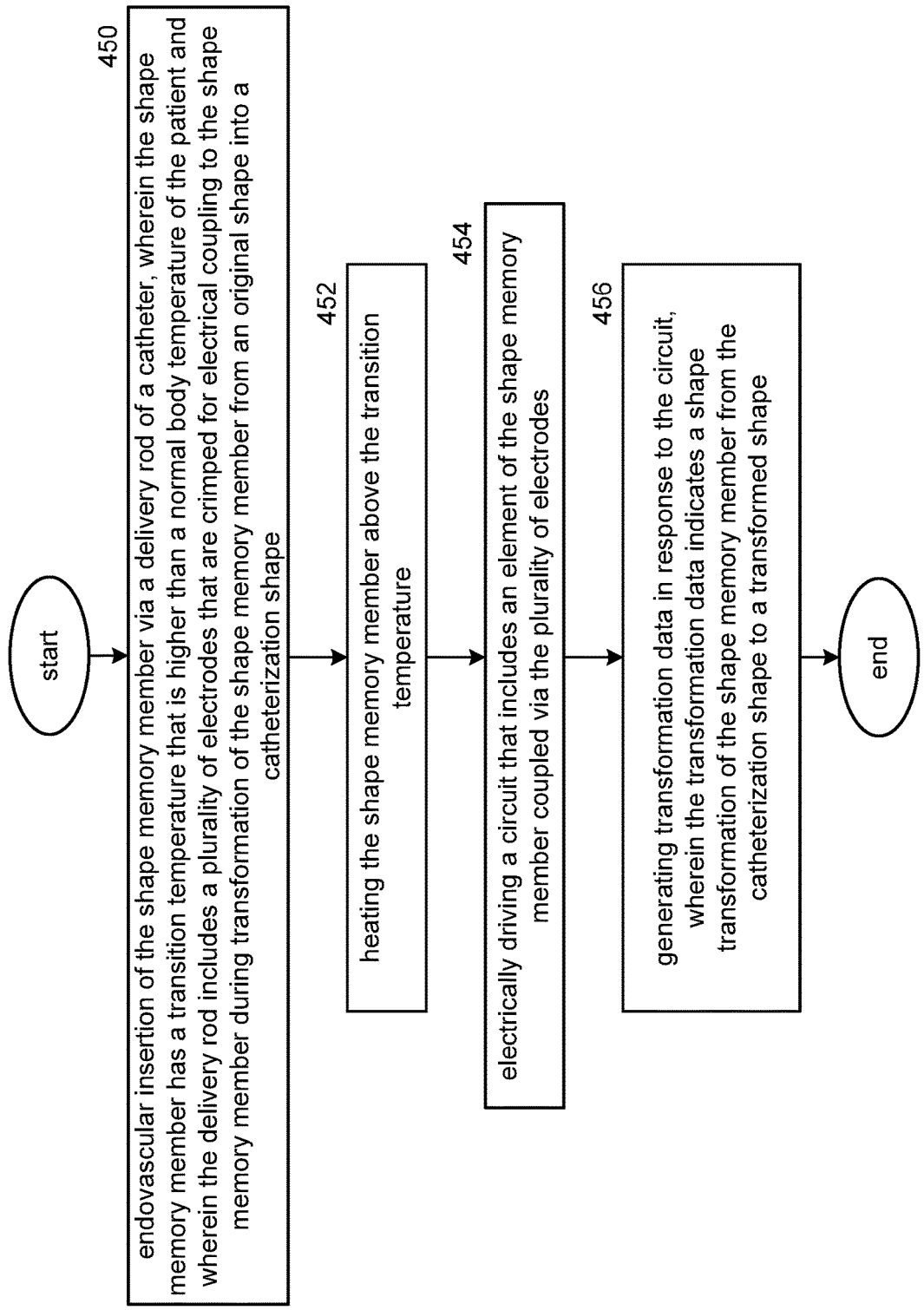
FIG. 29 is a flowchart representation of an embodiment of a method in accordance with the present invention.

FIG. 29 is a flowchart representation of an embodiment of a method in accordance with the present invention. In particular, a method is presented for use in conjunction with one or more features and functions described in conjunction with FIGS. 1-28. Step 450 includes endovascular insertion of a shape memory member via a delivery rod through a catheter, wherein the shape memory member has a transition temperature that is higher than a normal body temperature of the patient and wherein the catheter includes a plurality of electrodes that are crimped for electrical coupling to the shape memory member during transformation of the shape memory member from an original shape into a catheterization shape. Step 452 includes heating the shape memory member above the transition temperature. Step 454 includes electrically driving a circuit that includes an element of the shape memory member coupled via the plurality of electrodes. Step 456 includes generating transformation data in response to the circuit, wherein the transformation data indicates a shape transformation of the shape memory member from the catheterization shape to a transformed shape.

In an embodiment, the circuit is electrically driven by either a direct current or an alternative current. The shape memory catheterization device can include an endovascular stent for treating a blocked artery or an endovascular stent for treating an arterial aneurism. The shape memory catheterization device can intravenously deploy a drug in response to the shape transformation of the shape memory member from the catheterization shape to the transformed shape. The shape memory catheterization device can intravenously deploy a drug. The shape memory catheterization device can intravenously deploy a medical device in response to the shape transformation of the shape memory member from the catheterization shape to the transformed shape. The transformation data can include a data flag having a first value that indicates the catheterization shape and a second value that indicates the transformed shape.

FIG. 30 is a flowchart representation of an embodiment of a method in accordance with the present invention. In particular, a method is presented for use in conjunction with one or more features and functions described in conjunction with FIGS. 1-29. Step 460 includes heating a shape memory member above a transition temperature of the shape memory member, wherein the transition temperature that is higher than a normal body temperature of the patient. Step 462 includes crimping a plurality of electrodes of a catheter for electrical coupling to the shape memory member during transformation of the shape memory catheterization device from an original shape into a catheterization shape, while the shape memory catheterization device is above the transition temperature.

The shape memory catheterization device can include an endovascular stent for treating a blocked artery or an endovascular stent for treating an arterial aneurism. The shape memory catheterization device can intravenously deploy a drug in response to the shape transformation of the shape memory member from the catheterization shape to the transformed shape. The shape memory catheterization device can intravenously deploy a drug. The shape memory catheterization device can intravenously deploy a medical device in response to the shape transformation of the shape memory member from the catheterization shape to the transformed shape.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "operably coupled to", "coupled to", and/or "coupling" includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

As may also be used herein, the terms "processing module", "processing circuit", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

The present invention has been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "unit", also referred to as a "module", is used in the description of the various embodiments of the present invention. A module includes a processing module, a functional block, hardware, and/or software stored on memory for execution by a processing device that performs one or more functions as may be described herein. Note that, if the module is implemented via hardware, the hardware may operate independently and/or in conjunction software and/or firmware. As used herein, a module may contain one or more sub-modules, each of which may be one or more modules.

While particular combinations of various functions and features of the present invention have been expressly described herein, other combinations of these features and functions are likewise possible. The present invention is not limited by the particular examples disclosed herein and expressly incorporates these other combinations.

What is claimed is:

1. A system for deploying a shape memory catheterization device within a patient, the system comprising:
   a shape memory member having a transition temperature that is higher than a normal body temperature of the patient;
   a catheter having a delivery rod for endovascular insertion of the shape memory member;
   a heat source for heating the shape memory member above the transition temperature; and
   a transformation data generator, coupled to the catheter, that includes a circuit driver for driving a circuit that includes at least one strain gauge of the shape memory member and a detection circuit for generating transformation data based on a strain indicated by the strain gauge, wherein the transformation data indicates a shape transformation of the shape memory member from a catheterization shape to a transformed shape.

2. The system of claim 1 further comprising:
   a heating control generator, coupled to the transformation data generator and the heat source, the heating control generator generating a control signal for controlling the heat source based on the transformation data.

3. The system of claim 2 wherein the heating control generator generates the control signal to discontinue the heating of the shape memory member when the transformation data indicates the shape transformation of the shape memory member from the catheterization shape to the transformed shape.

4. The system of claim 1 wherein the detection circuit generates the transformation data to indicate the shape transformation of the shape memory member from the catheterization shape to the transformed shape when the strain compares favorably to a transformation threshold.

5. The system of claim 1 wherein the shape memory catheterization device includes an endovascular stent for treating a blocked artery.

6. The system of claim 1 wherein the shape memory catheterization device includes an endovascular stent for treating an arterial aneurism.

7. The system of claim 1 wherein the shape memory catheterization device intravenously deploys a drug in response to the shape transformation of the shape memory member from the catheterization shape to the transformed shape.

8. The system of claim 1 wherein the shape memory catheterization device intravenously deploys a drug.

9. The system of claim 1 wherein the shape memory catheterization device intravenously deploys a medical device in response to the shape transformation of the shape memory member from the catheterization shape to the transformed shape.

10. The system of claim 1 wherein the transformation data includes a data flag having a first value that indicates the catheterization shape and a second value that indicates the transformed shape.

* * * * *